US00PP11002P

United States Patent [19]

Mak

[11] Patent Number: Plant 11,002

[45] Date of Patent: Jul. 6, 1999

[54] LILIUM "SOIREE"

[76] Inventor: Johan A. Mak, 5595 Halls Ferry Rd., Independence, Oreg. 97351

[21] Appl. No.: 08/766,283

[22] Filed: Dec. 13, 1996

[51] Int. Cl.[6] ..... A01H 5/00

[52] U.S. Cl. ..... Plt./87.4

[58] Field of Search ..... Plt./87.4

*Primary Examiner*—James R. Feyrer
*Assistant Examiner*—Elizabeth C. Kemmerer

[57] ABSTRACT

A new variety of hybrid lily plant bearing semi-upright flowers of excellent form and long persistence, both on the plant and as cut-flowers. The flowers of the new plant are particularly characterized by their deep red coloration at the edge shading into a wide yellow orange area surrounding a small dark brown ray extending from the nectary furrows. This combination is completely new in the Asiatic hybrid divisions of lilies suited to forcing and to mass commercial cultivation. The variety is highly resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 't Zand, Netherlands, in 1989. The breeding efforts had as their objective the production of large-flowered Asiatic hybrids in bicolored combinations of red, yellow, and orange, with pigmented papillae, its flowers in upright position, suited to forcing into flower out of season, heretofore unknown in the lily breeding art.

I achieved the desired objective by intercrossing selected semi-upright red, yellow and bicolored Asiatic seedlings suited to forcing for year-round use as cut-flowers and carrying the recessive gene for bi-colors.

The flowers of my new lily are characterized by large size and broad-tepalled "bowl-shaped" form, unusually thick substance, and deep red coloration shading into a yellow orange wide area which surrounds a small dark brown ray extending from the nectary furrows. It possesses unusually strong, stout stems. In addition, the clone possesses to a high degree desirable characteristics of hybrid vigor. The clone is a good grower and propagator, as observed at 't Zand, Netherlands, and at Salem, Oreg.

My new variety of lily plant has been asexually reproduced by me and under my direction at 't Zand, Netherlands, and at Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWINGS

My new variety of lily plant is illustrated in the two accompanying photographic drawings, which shows the open bloom in full color and illustrates the flower form, the tepal arrangement, and in particular the novel and distinctive flower coloration with its deep red coloration at the edge shading into a wide yellow orange area surrounding a small dark brown ray extending from the nectary furrows, with pigmented papillae and its flowers in upright position.

DESCRIPTION OF THE NEW VARIETY

The following is a detailed description of my new variety of Oriental hybrid lily, with nomenclature according to the *International Lily Register* (Royal Horticultural Society of London, Second Edition, 1969), and with color designations according to the Colour Chart of The Royal Horticultural Society, published by the Society in 1966.

The Plant

Origin: Seedling.

*Seed parent.*—(Connecticut Red×Selected unnamed Seedling)×Roter Cardinal.

*Pollen parent.*—Avignon.

Commercial classification: Hybrid *Lilium* clone.

Horticultural classification: Division 1-A, upright Asiatic hybrid lily, according to the Horticultural Classification of Lilies, Royal Horticultural Society of London.

Form: Single stem, erect and stately.

Height: 75 to 135 cm from bulbs 14 to 18 cm in circumference, provided their light levels are adequate; low light levels may cause "stretching."

Growth: Vigorous and upright.

Foliage quantity: Abundant.

Shape of leaf: Lanceolate (pointed).

Texture: Leathery and glossy.

Color: Deep green, lighter on lower side.

Bulb size: Any size, ranging to 25 cm circumference commercially.

Bulb color: White, with flushes of pink or yellow after exposure to light.

The Bud

Form: Obtuse, ovoid, and long.

Size: 7 to 10 cm long and 7 to 9 cm in circumference just prior to opening.

Opening: Bud opens slowly, in response to morning light; this takes about one hour.

Color: Close to R.H.S. C.C. Red Group 45A.

Peduncle: Averages 10 to 15 cm, but it may elongate if light levels are too low or if bulbs have been improperly stored prior to forcing. Color is very dark green.

The Flower

Blooming habit: Annually in midseason; flowers once and profusely.

Size: Flowers are medium large-sized, averaging 12 to 17 cm in diameter, the outer tepals are 2.5 to 3.25 cm wide, and the inner tepals are 3.5 to 5 cm wide.

Borne: In a single racemic inflorescence producing 7 to 10 flowers from a bulb 14 to 16 cm in circumference.
Shape: Form a bowl shape by the second day after opening.
Tepalage: Typical of genus *Lilium*, with 6 imbricated tepals.
Tepal color: Edge is R.H.S. C.C. Red Group 42A–42B and the yellow Center is R.H.S. C.C. Yellow Orange 15A–17B.
Inner base of tepal: R.H.S. C.C. Red Group 43A.
Tepal spotting: The basal half of each tepal is spotted with magenta rose (R.H.S. C.C. Red 43A) papillae of moderate size.
Tepal longevity: Tepals stay on stems about three weeks.
Pedicel length: Average 7 to 12 cm long.
Pedicel color: Dark green with dark plum overlay.
Pedicel form: Sturdy and ascending.
Appearance: Flower is shiny.
Disease resistance: The flower and plant are resistant to disease; in particular, they are resistant to Fusarium bulb rot and Botrytis blight.
Fragrance: None.
Lasting quality: The flower is long lasting, both on the plant and as a cut-flower.

The Reproductive Organs

Stamens: Arrangement typical of genus *Lilium*. Six stamens with soft green to palest pink filaments 5 to 7 cm long.
Pollen and anthers (dehisced): R.H.S. C.C. Orange Red Group 34A.
Pistil: One in number, 7 to 9 cm long.
Stigma: R.H.S. C.C. Orange red group 33A.
Characteristics of ovary: Characteristic of genus *Lilium*.

The Fruit

Fertility: The fruit bears fertile seed.
Shape: Ovoid.
Color at maturity: Soft brown, sometimes overlaid with soft plum.

My new variety of Asiatic hybrid lily most nearly resembles "Esther", but it has bigger flowers which are darker red and its stem is much darker.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower producer from pre-cooled bulbs forced under glass out of season; and in particular by its unique semi upright-facing flowers with its deep red coloration at the edge shading into a wide yellow orange area surrounding a small dark brown ray extending from the nectary furrows and its dark stem, a combination unique among Asiatic hybrid lilies suited for to forcing and to mass commercial cultivation.

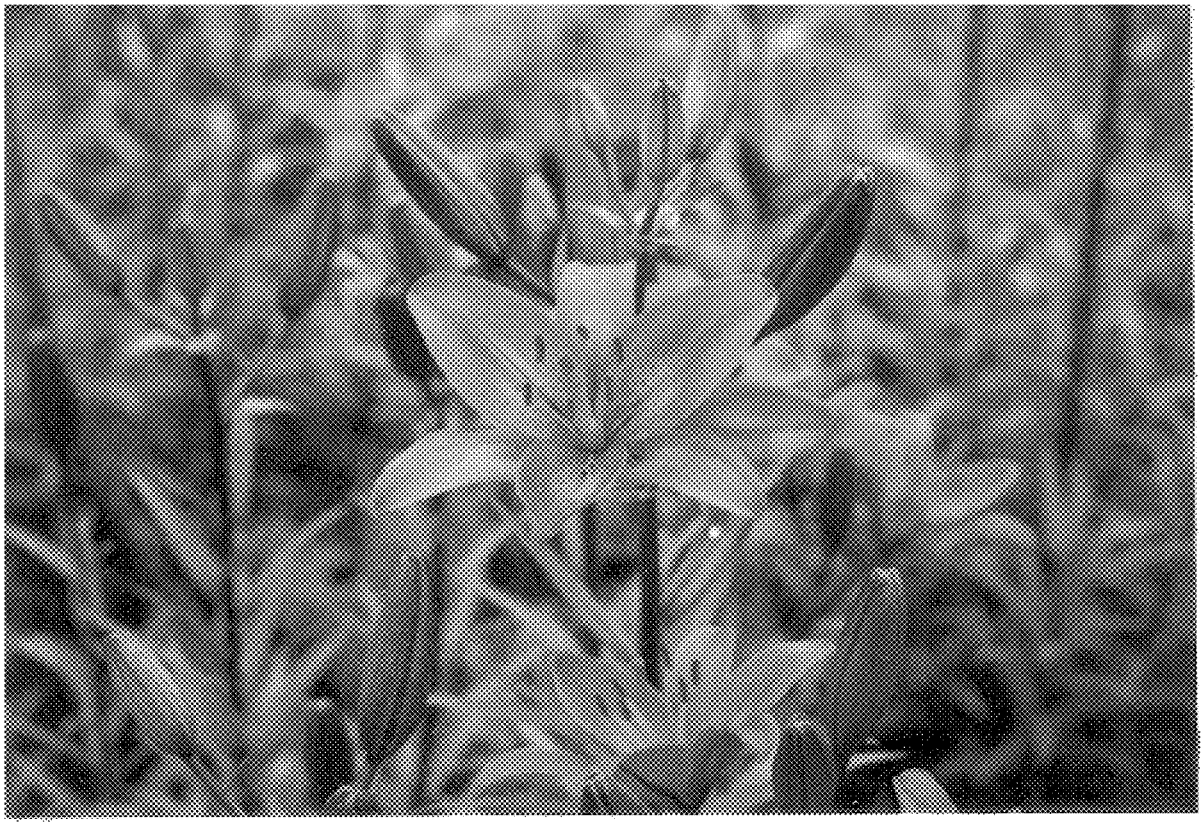
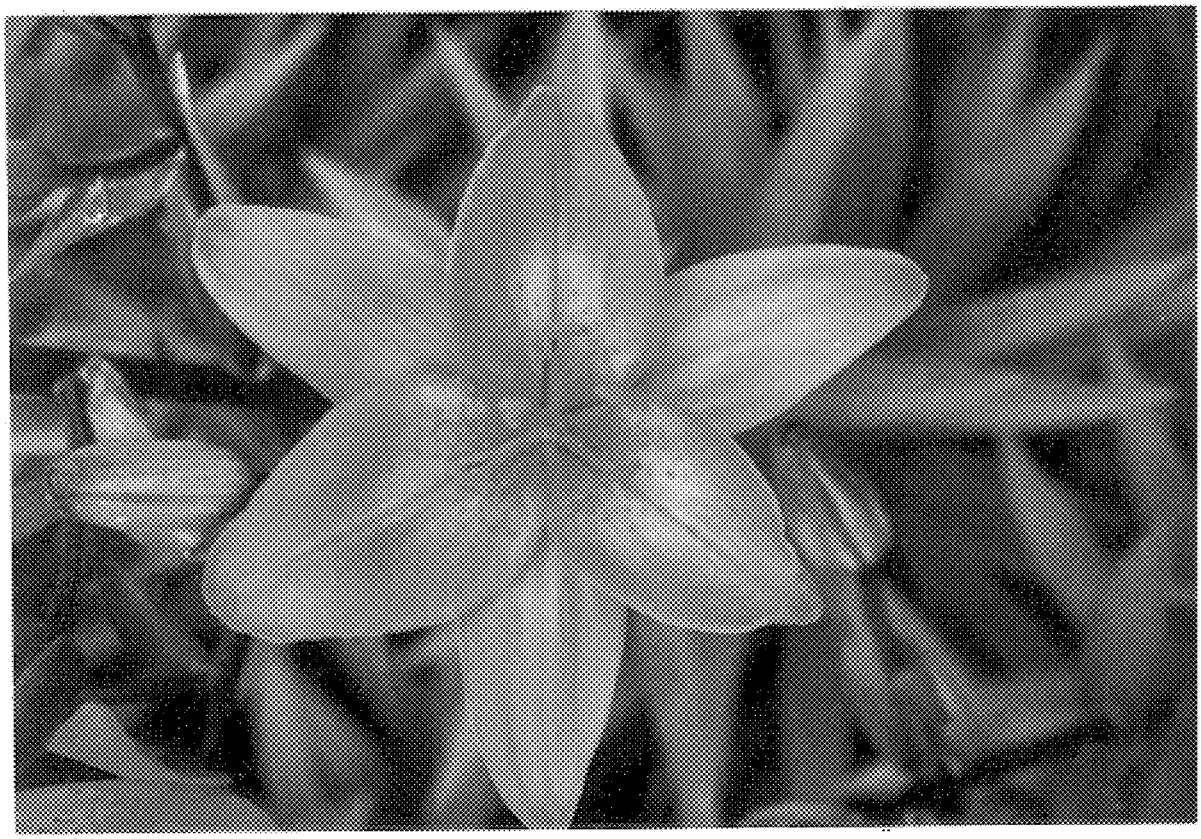

* * * * *